United States Patent [19]

Lopez et al.

[11] Patent Number: 4,749,553
[45] Date of Patent: Jun. 7, 1988

[54] BREATH ALCOHOL DETECTOR WITH IMPROVED COMPENSATION FOR ENVIRONMENTAL VARIABLES

[75] Inventors: Benjamin L. Lopez, Westminster; Steven A. Beard, Denver; Kirby Phillips, Lakewood, all of Colo.

[73] Assignee: Life Loc, Inc., Wheatridge, Colo.

[21] Appl. No.: 35,758

[22] Filed: Apr. 8, 1987

[51] Int. Cl.$^4$ .............................................. G01N 1/14
[52] U.S. Cl. ........................................ 422/84; 73/23; 73/27 R; 128/719; 180/272; 340/53; 340/576; 436/132; 436/900
[58] Field of Search ................. 73/23, 27 R; 128/719; 180/272; 340/53, 576; 422/84, 85; 436/132, 900

[56] References Cited

U.S. PATENT DOCUMENTS

| | | | |
|---|---|---|---|
| 3,275,975 | 9/1966 | King | 180/272 |
| 3,780,311 | 12/1973 | Brown | 307/10 R |
| 3,815,087 | 6/1974 | Hirano et al. | 340/53 |
| 3,818,434 | 6/1974 | Gotoh et al. | 340/53 |
| 3,823,382 | 7/1974 | Gaddy | 340/53 |
| 3,831,707 | 8/1974 | Takeuchi | 180/99 |
| 3,855,573 | 12/1974 | Honda et al. | 340/53 |
| 4,039,852 | 8/1977 | Miyamoto et al. | 307/326 |
| 4,592,443 | 6/1986 | Simon | 180/272 |
| 4,613,845 | 9/1986 | Du Bois | 340/576 X |
| 4,617,821 | 10/1986 | Yokoyama et al. | 73/23 |

Primary Examiner—David L. Lacey
Assistant Examiner—Michael S. Gzybowski
Attorney, Agent, or Firm—John R. Ley

[57] ABSTRACT

A breath alcohol detector measures and compensates for distance between the mouth of the individual exhaling breath into the ambient air and the detector, the atmospheric pressure, and the temperature. Blood alcohol content information is calculated using these compensation factors and a signal obtained from an electrochemical fuel cell which is indicative of the amount of alcohol or other gas contained in the sample. The detector also includes a reciprocally acting electromagnetically energized motor which drives a diaphragm pump to draw the sample into the electrochemical fuel cell.

16 Claims, 6 Drawing Sheets

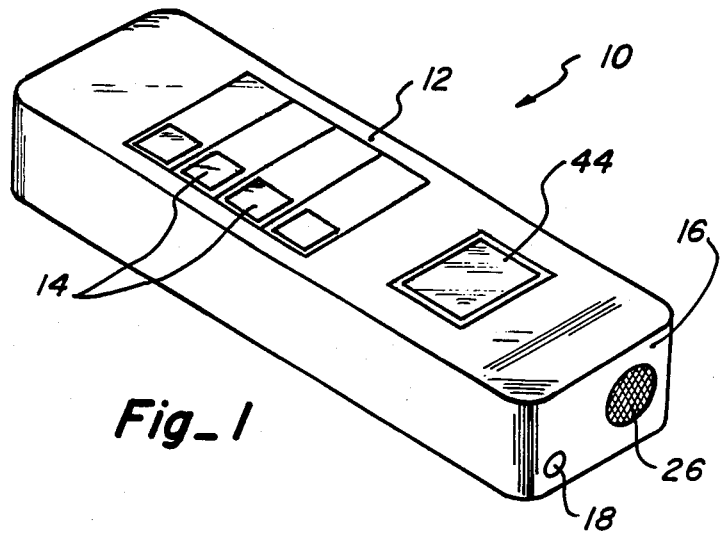
Fig_1
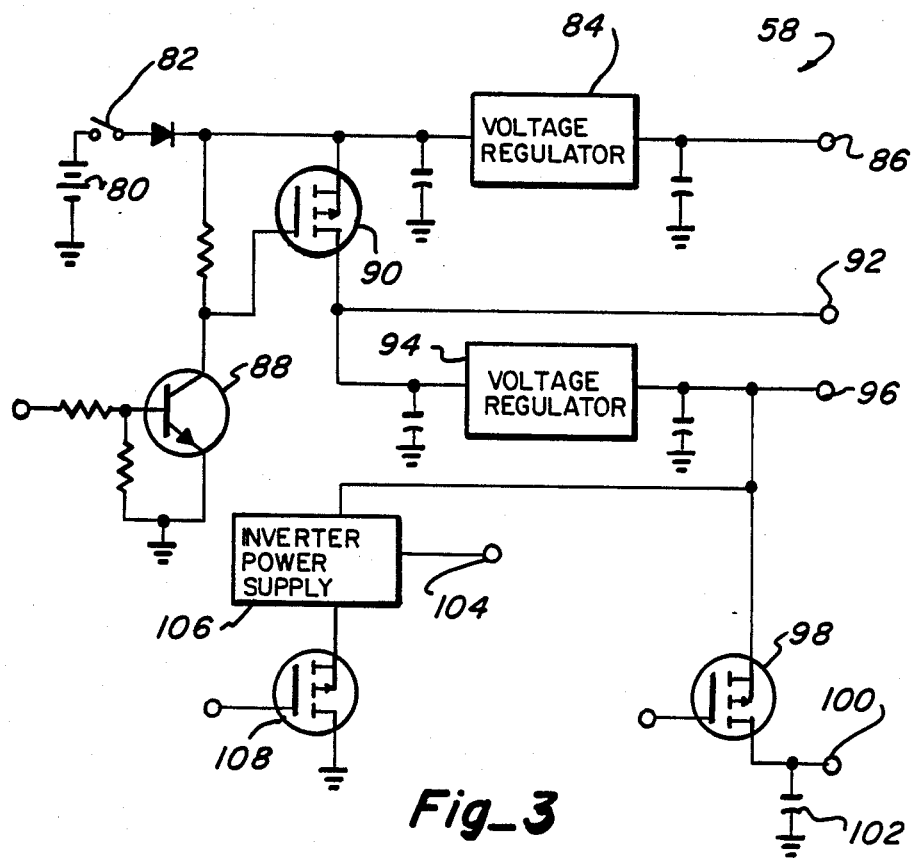
Fig_3

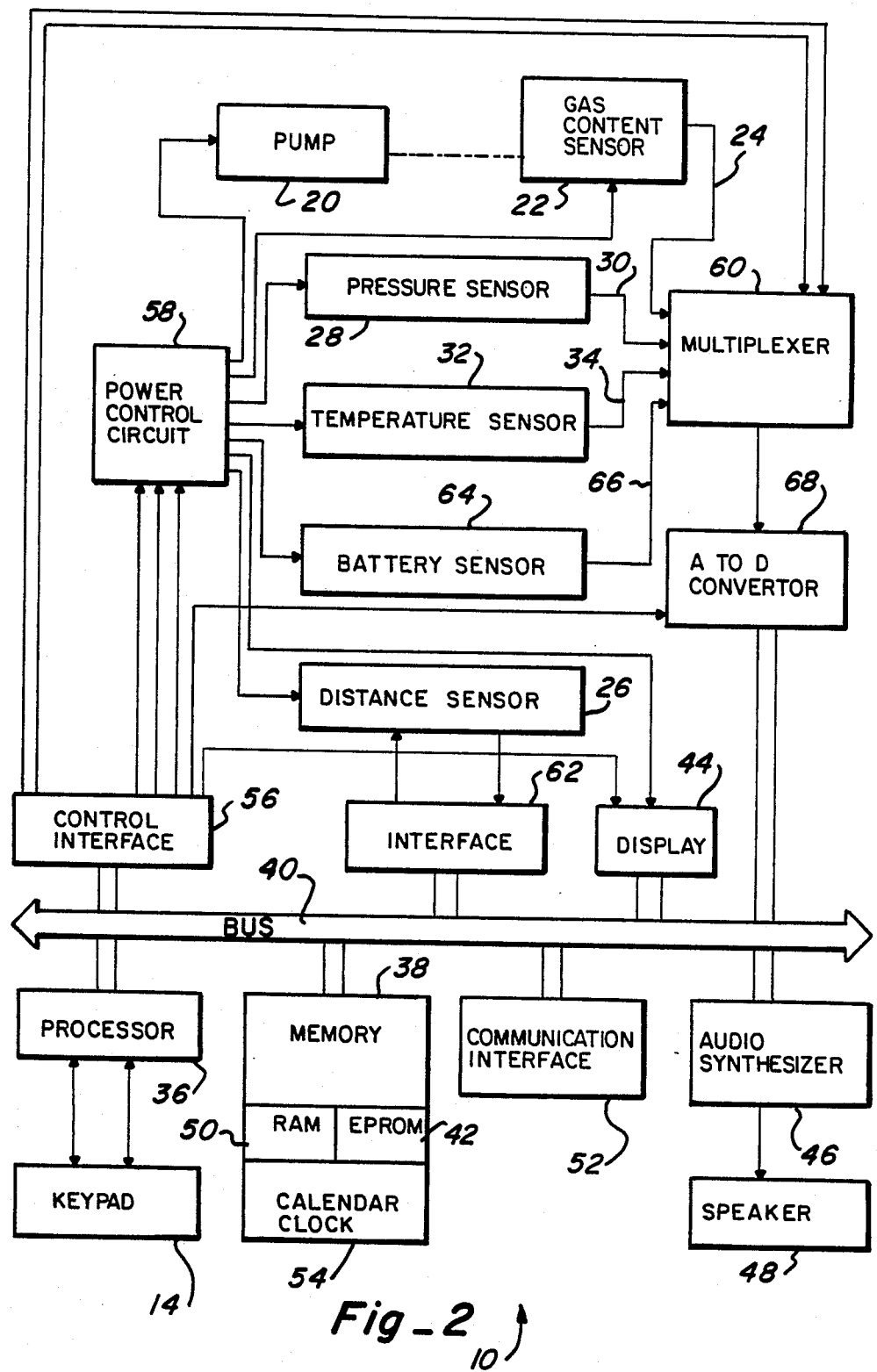
Fig_2

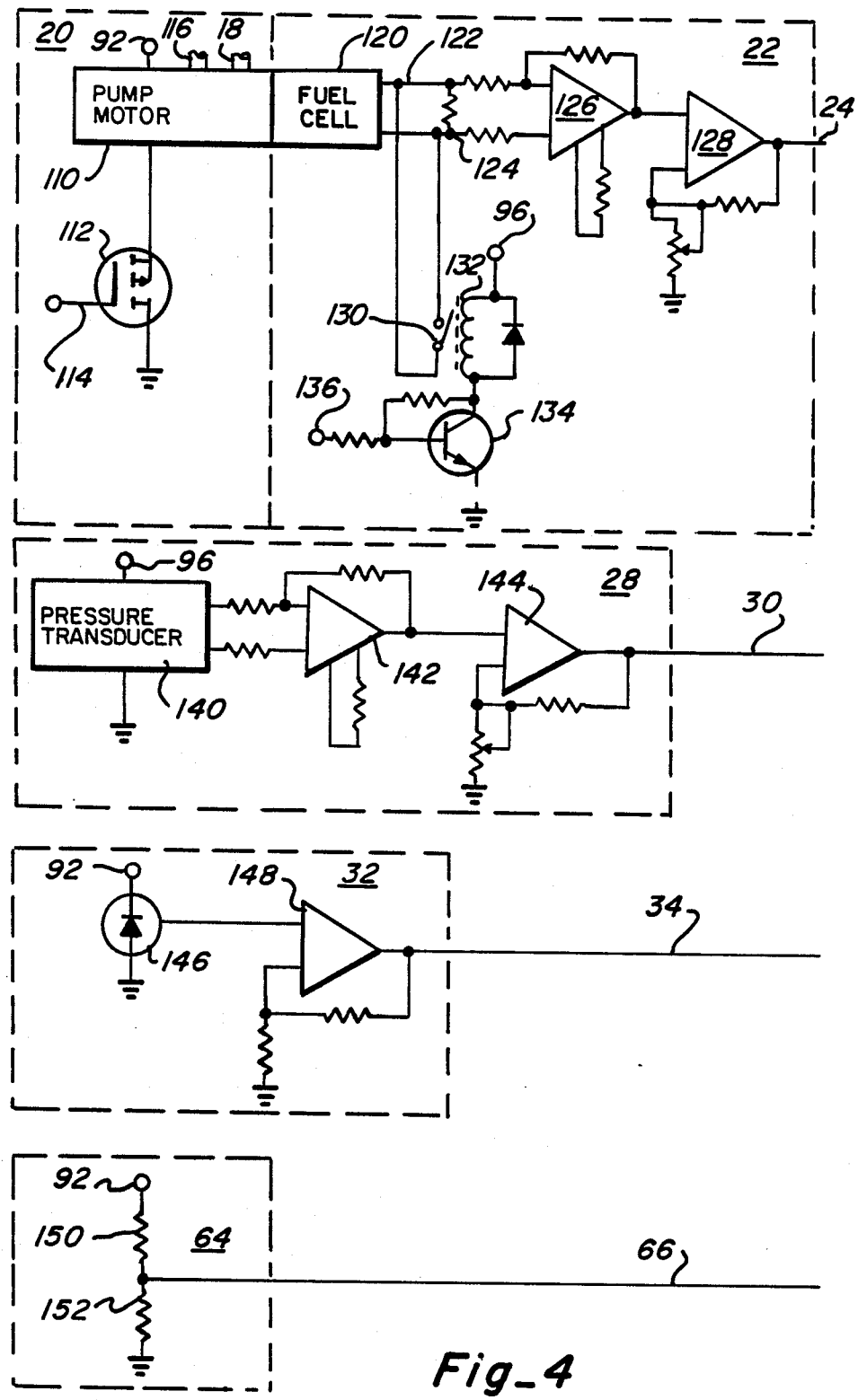
Fig_4

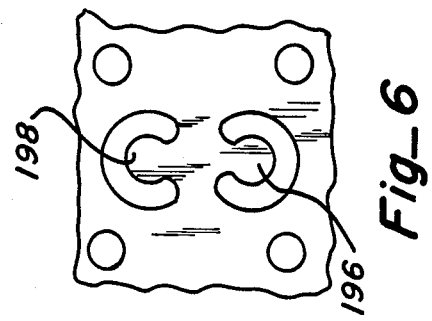
Fig_6
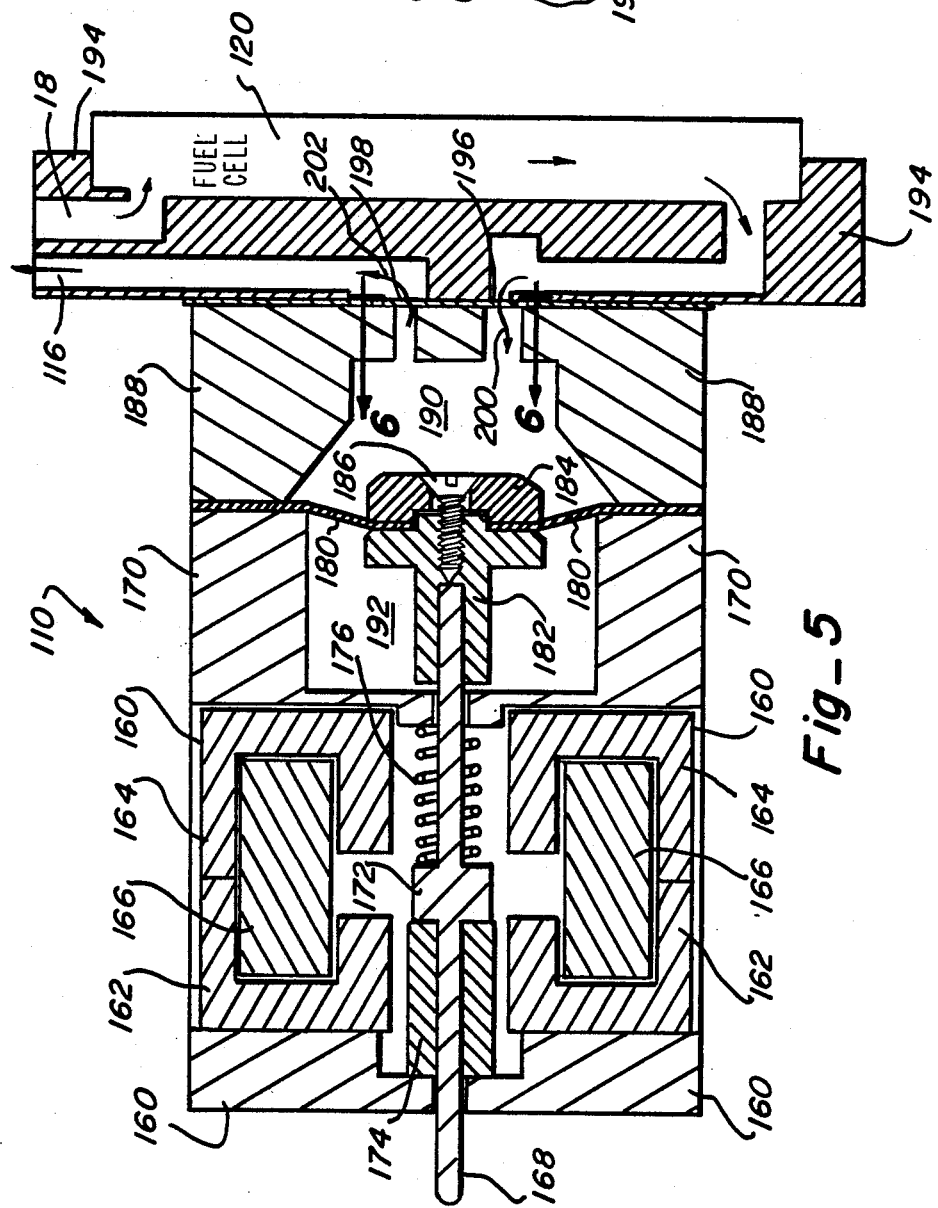
Fig_5

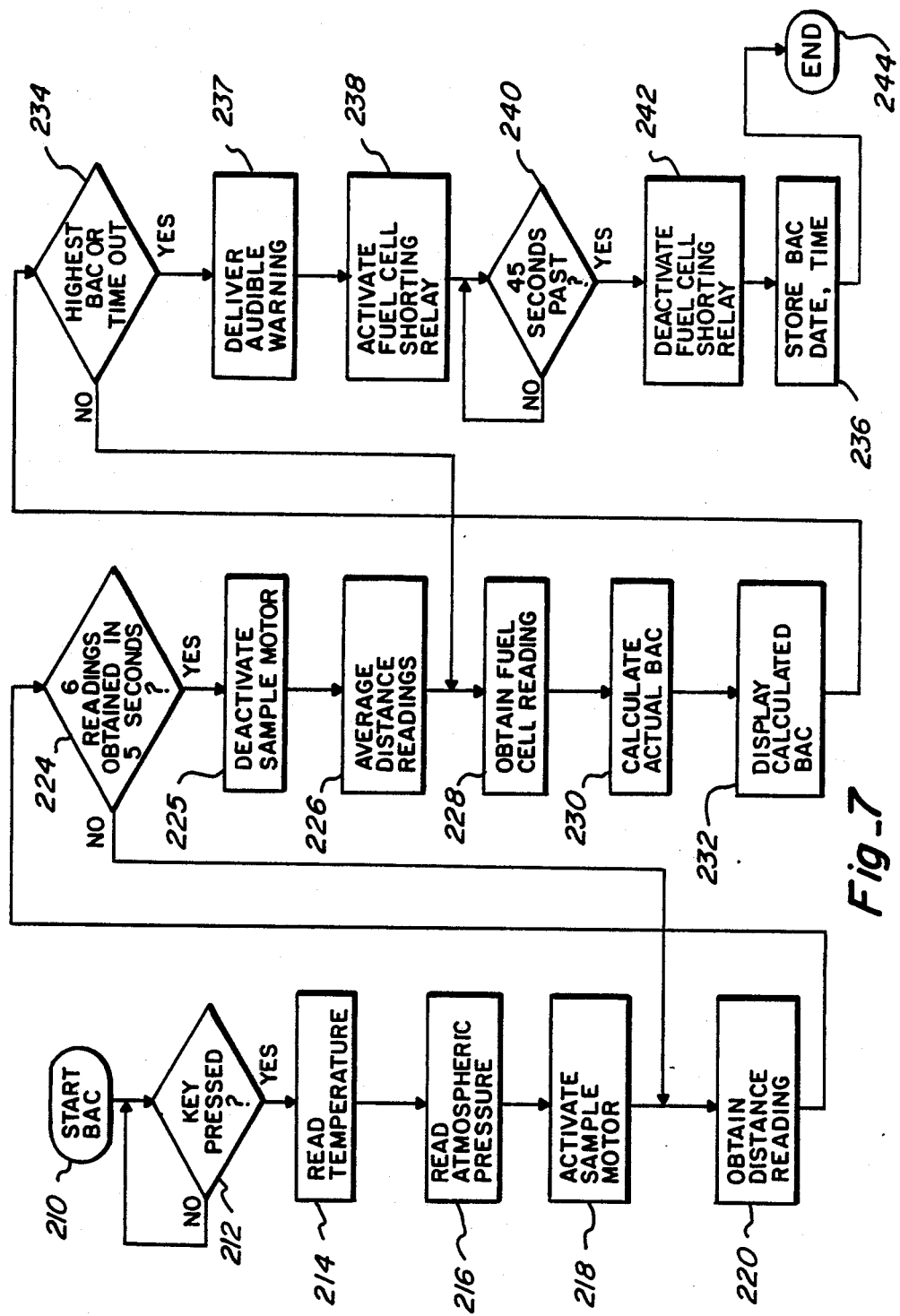

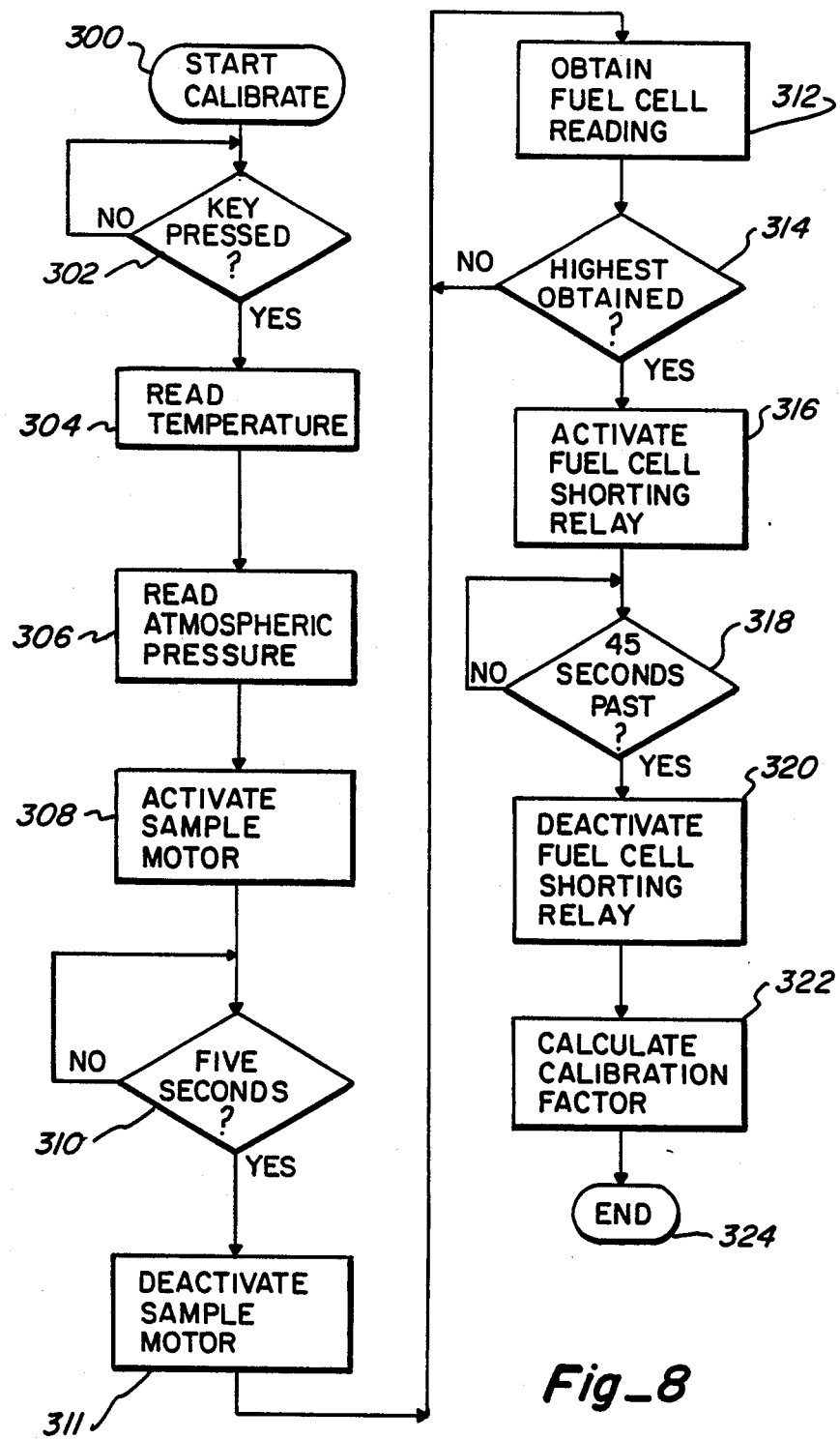
Fig_8

BREATH ALCOHOL DETECTOR WITH IMPROVED COMPENSATION FOR ENVIRONMENTAL VARIABLES

This invention pertains to a new and improved breath alcohol detector capable of obtaining reliable data indicating blood alcohol concentration (BAC), as a result of a non-intrusive analysis by sampling the breath alcohol content. The subject is not required to breathe directly into a collection tube or device. Environmental variables such as distance, dispersion, diffusion, temperature, and atmospheric pressure are compensated. More precise and better flow regulation of the breath sample through a gas content sensor is established. Further improvements include recording data for later use and informing the subject of the test results and other relevant information relating to the test results.

BACKGROUND OF THE INVENTION

A variety of different techniques are available for determining the state of intoxication or lack thereof of individuals. Some techniques are medically based, and involve drawing a sample of blood which is then analyzed. Other techniques require a person to exhale a deep lung breath sample directly into a breath sampling device or breathalyzer. The breathalyzer detects and measures the presence and concentration of alcohol (ethanol) in the exhaled breath sample, and correlates the measured alcohol content to a blood alcohol concentration in the individual. By requiring that the individual exhale directly into the breathalyzer, the breath sample is more accurately related to the alcohol content of the gas within the lungs, and consequently the blood alcohol content. Measuring the alcohol content of the directly exhaled breath sample also reduces the problems of having to account for and correct various variables which introduce errors in measurement.

Although not intrusive into the physical body of the individual subjected to the test, the person must directly interact with the breathalyzer when exhaling the lung gas sample into the machine. Such interaction is usually considered offensive or embarrassing, and people will not normally voluntarily submit to such tests unless such tests are enforced by law enforcement authorities. Enforced breathalyzer tests are usually carried out in police stations or other locations where the breathalyzer is permanently located, because most breathalyzers are sensitive to a wide variety of destabilizing effects. It is considered better practice to avoid moving the breathalyzers than to subject them to situations which could alter their calibration, particularly since the breath alcohol content data obtained from such machines might be used as evidence in legal proceedings.

Other types of breathalyzer devices are known which function in response to breath samples that have not been exhaled directly into the device. Such devices are generally not considered reliable, because of the significant differences between the measured alcohol content and the actual blood alcohol content of the individual giving the breath sample. The inaccuracy in such machines generally results from a failure or inability to account for important environmental and other variables which can significantly influence the breath alcohol content data obtained.

In addition to the most common uses of breathalyzers by law enforcement authorities, there is an increasing demand for use of breathalyzers in private enterprise. For example, owners of liquor serving establishments may wish to check the condition of their patrons before serving further liquor to them, to avoid potential legal liability for the acts committed by the patrons while intoxicated. Employers may wish to test the condition of their employees to detect deficiencies in performance. Medical authorities in alcohol treatment centers may wish to monitor the condition of their patients. Even law enforcement authorities would find a portable, non-invasive breathalyzer which does not require the person to directly exhale into it and which still delivers accurate data, a substantial benefit and assistance in their duties of determining whether a suspect is intoxicated. These examples of potential uses all require, or consider desirable, a small portable breathalyzer which does not require the individual to breath directly into it, but yet still obtains a very high degree of accuracy in the measured breath alcohol content.

SUMMARY OF THE INVENTION

In accordance with its major aspects, the breath alcohol detector of the present invention obtains blood alcohol concentration information from a sample of breath exhaled from an individual into ambient air. The detector comprises means for collecting the sample of exhaled breath which has been diffused into the ambient air and means for deriving an alcohol content signal related to the quantity of alcohol present in the collected sample. The detector also includes means for deriving a distance signal related to the distance at which the sample was collected from the mouth of the individual, thereby compensating for diffusion of the exhaled breath into the ambient air. The detector also includes a means for deriving a temperature signal related to the temperature of the ambient air, and means for deriving a pressure signal related to the atmospheric pressure at the location where the sample was collected. A blood alcohol content value is calculated using the alcohol content signal, the distance signal, the temperature signal and the pressure signal, by an algorithm contained in memory of a computer associated with the detector. In addition to compensating for diffusion by measuring the distance between the detector and the mouth of the individual exhaling, the temperature signal allows for compensation of the buoyancy effect of the warm exhaled breath into the generally cooler ambient air, and the pressure signal compensates for the varying amount of oxygen in the ambient air according to the altitude where the detector is employed. The compensation for varying amounts of oxygen is important in that recalibration of the unit is not generally required, but if it is required, the detector provides a self-calibration routine for conveniently accomplishing recalibration.

In accordance with another aspect of the present invention, a new and improved pump draws the sample of breath exhaled into the ambient air into an electrochemical fuel cell within the detector. The improved pump includes a reciprocally acting motor means which includes a shaft retained for reciprocal movement and an electromagnetic means positioned relative to the shaft for moving the shaft in opposite directions of reciprocal movement. A diaphragm is operatively connected to the shaft and is deflected upon reciprocal movement of the shaft. The diaphragm is included within a pumping chamber, and one way valves control the inlet and exhaust flow of fluid into and out of the pumping chamber in relation to the positive and negative pressures created by deflection of the diaphragm.

The present invention can be better appreciated by reference to the following detailed description of a preferred embodiment of the present invention, which is also illustrated in the accompanying drawings that are described below.

BRIEF DESCRIPTION OF THE DRAWINGS

FIG. 1 is a perspective view of a breath alcohol detector of the present invention.

FIG. 2 is a block diagram of the components of the breath alcohol detector shown in FIG. 1.

FIG. 3 is a schematic and block diagram of a power control circuit shown in FIG. 2.

FIG. 4 is a schematic and block diagram of a pump, a gas content sensor, a pressure sensor, a temperature sensor and a battery sensor shown in FIG. 2.

FIG. 5 is a sectioned side view of a pump motor shown in FIGS. 2 and 4.

FIG. 6. is a section view taken substantially in the plane of line 6—6 of FIG. 5.

FIG. 7 is a flow diagram illustrating the operation of the breath alcohol detector shown in FIG. 2.

FIG. 8 is a flow diagram illustrating the operation for calibrating the breath alcohol detector shown in FIG. 2.

DETAILED DESCRIPTION OF THE PRESENTLY PREFERRED EMBODIMENT

A presently preferred embodiment of the breath alcohol detector of the present invention is illustrated by reference numeral 10 in FIGS. 1 and 2. The detector 10 is preferably enclosed in a relatively small housing 12 which allows the detector 10 to be held in the hand of the operator. The detector 10 includes a command key pad 14 for generating signals which control the operation of the detector 10. In order to obtain a breath sample from which the alcohol content can be determined, the housing 12 of the detector 10 is pointed with its front end 16 toward the mouth of an individual undergoing the test. In the front end 16, an inlet port 18 is formed. The inlet port 18 is connected to a pump 20 which draws the sample of exhaled breath into a gas content sensor 22. The gas content sensor 22 delivers a signal at 24 which is indicative of the content of alcohol (ethanol) in the sample of breath exhaled into the ambient air and drawn into the detector 10.

A distance sensor 26 is also positioned in the front end 16 of the housing 12. The distance sensor 26 is used to measure the distance between the detector 10 and the mouth of the individual exhaling sample which is drawn into the input port 18.

A pressure sensor 28 is also located within the housing 12. The pressure sensor 28 derives a signal at 30 which is directly related to the atmospheric pressure.

A temperature sensor 32 is positioned within the housing 12, preferably at a location to respond to the temperature of the ambient air. The temperature sensor 32 supplies a temperature signal at 34 which is directly related to the temperature which it senses.

A micro computer is also enclosed within the housing 12 of the detector 10. The computer includes a conventional processor 36, a conventional main memory 38, and a bus 40 which interconnects the various computer and other interface components of the detector 10. The signal supplied by the distance detector 26, which contains information about the distance from the detector to the individual's mouth, is converted to a distance value, according to a distance algorithm that is executed by the computer according to a program stored in an electrically programmable read only memory 42 (EPROM) component of the main memory 38. Data from the distance sensor 26, the gas content sensor 22, the pressure sensor 28 and the temperature sensor 32 are further processed according to a BAC algorithm stored in main memory, to obtain a value of probable BAC.

The BAC information can be displayed, under control of the key pad 14, at a display 44 of the detector 10. The key pad 14 and display 44 are readily visible to the operator when the detector 10 is held in the operator's hand. In addition to displaying the BAC information at the display 44, the detector 10 may optionally include an audio synthesizer 46 connected to a speaker 48 which creates aural warnings appropriate to the BAC information. The audible warnings are particularly useful when the detector 10 is mounted in an automobile to alert the driver of unacceptable conditions, but have other applications as well.

The BAC information can also be stored in memory, such as random access memory (RAM) 50 of the main memory 38, for later retrieval and use by law enforcement authorities or others. When later retrieved, the BAC information can be displayed at the display 44 and/or it can be uploaded or transferred from a conventional computer communications interface 52 onto another computer or other device receptive of this information, for example. The time and date when the BAC information was collected, may be identified by use of a calendar clock 54, which is also included within the main memory 38 of the detector 10.

The overall operation of the detector 10 is controlled by the processor 36 and the operating program stored in the memory 38. A control interface 56 is provided for deriving control signals for a power control circuit 58, a multiplexer 60, an analog to digital converter 68 and the display 44, in response to the digital signals applied over the conventional address and data conductors of the bus 40. The control interface 56 includes a conventional programmable logic device (PLD), which has been programmed to recognize the particular pattern of signals on the address and data conductors of the bus 40 according to each control function desired, and in response, to supply the individual control signals to the components mentioned. In this manner, digital signals applied on the bus 40 under the control of the processor 36 control the display 44, the A to D converter 68, the multiplexer 60, and the power control circuit 58.

Similarly, the distance detector 56, which is preferably a conventional ultrasonic sonar ranging device such as that manufactured by Polaroid Land Corp., includes its own interface 62. The function of the interface 62 is to recognize the digital signals on the address and data conductors of the bus 40 and deliver drive control signals to the distance sensor 26, and convert echo signals supplied from the sensor 26 into digital signals applied to the bus 40. In the case of a sonar ranging device, the interface 62 delivers the drive signal to the transducer disc (not shown) of the sensor 26 so it functions as a transmitter for transmitting the ultrasonic waves. After transmitting, the transducer disc becomes a receiver to sense the reflected ultrasonic wave. The reflected wave is converted by the transducer disc into an echo signal which is supplied to the interface 62. The interface 62 converts the echo signal into digital form and supplies it over the bus 40. The echo signal created by the reflected wave establishes a relative time between transmitting the wave and receiving its reflection, and this relative time is employed as a variable in the distance algorithm to establish the distance information. The interface 62 is a conventional buffer device.

Another sensor included within the detector 10 is a low battery voltage sensor 64. The battery sensor 64 monitors the voltage of a battery which powers the detector, and delivers a low battery signal at 66 when the voltage of the battery falls below a predetermined level. The separate power control circuit 58 is provided to energize the pump 20, the sensors 22, 26, 28, 32 and 64 only when it is necessary that each of these elements function. In this manner, battery energy is conserved. Signals from the control interface 56 cause the power control circuit 58 to energize the appropriate pump or sensor at the appropriate time.

The signals from the sensors 22, 28, 32 and 64 are all analog signals. The multiplexer 60, under the control of the control interface 56, selects a predetermined sequence of signals 24, 30, 34 and 66 from the sensors 22, 28, 32 and 64, respectively, and supplies the selected signal to a conventional analog to digital converter 68. The converter 68, under the control of the interface 56, converts the selected signal into digital form and applies it to the bus 40. Control signals supplied by the control interface 56 operatively select the one of the four input signals which is to be converted into digital form.

Details of the power control circuit 58 are illustrated in FIG. 3. Electrical power for the detector 10 is supplied by a battery 80. An on-off switch 82 is provided to energize the detector. When the switch 82 is closed, a voltage regulator 84 provides a regulated voltage for all of the digital computer components, the control circuitry, the interfaces and other circuitry. This regulated voltage is applied at terminal 86. When it is desired to selectively energize the pump and sensors, the signal which is normally supplied by the control interface 56 (FIG. 2) to the base of transistor 88 is removed, thereby turning transistor 88 off and turning transistor 90 on. With transistor 90 turned on, power from the battery 80 is also supplied directly to a terminal 92. The terminal 92 supplies electrical power to the pump 20, the pressure sensor 32 and the battery sensor 64 (FIGS. 2 and 4). Power is also supplied to a voltage regulator 94. The voltage level at the output terminal 96 of the voltage regulator 94 is at a regulated lower voltage than that present at terminal 92. The voltage level at terminal 92 is applied to the pressure transducer 28 (FIGS. 2 and 4).

In order to energize the distance sensor 26 (FIG. 2) transistor 98 is switched on by signals from the control interface 56 (FIG. 2). The voltage level at the terminal 96 is thus applied at terminal 100. A storage capacitor 102 acts as a stabilizing storage capacitor and supplies the instantaneous high surge current requirements when activating the ultrasonic transducer disc of the distance detector. Thus, when the distance sensor requires current, the capacitor 102 as well as the voltage regulator 94 deliver that current, with the instantaneous high demand being supplemented by the capacitor 102. A relatively high level of voltage is available at terminal 104 from an inverter power supply 106, when transistor 108 is turned on. The relatively high voltage level at terminal 104 is applied to the display 44 (FIG. 2) to supply back light for the display. Transistor 108 is turned on by signals supplied by the control interface 56 (FIG. 2).

Details of the pump 20, the gas content sensor 22, the pressure sensor 28, the temperature sensor 32 and the battery sensor 64 are illustrated in FIG. 4.

The pump 20 includes a pump motor 110 which is shown in mechanical detail in FIGS. 5 and 6. As will be discussed subsequently, the pump motor 110 is electrically operated from the source of electrical power at terminal 92. A transistor 112 selectively conducts pulses of current through the pump motor 110, in response to signals applied at terminal 114 from the control interface 56 (FIG. 2). The pump motor 110 includes the inlet port 18 (also see FIG. 1) where the sample is drawn in. Gas is exhausted from the pump motor 110 through an outlet port 116.

The gas content sensor 22 includes an electrochemical fuel cell 120. The fuel cell 120 receives the sample of gas which is drawn in through the inlet port 18 by the pump motor 110. The gas sample passes through the cell 120 and is exhausted from the outlet port 116. The fuel cell 120 is an electrochemical cell of the type sold by Intoximeters, Inc. of St. Louis, Mo. and Dreagerwerk, A. G. of West Germany. A variety of different types of fuel cells may be employed, but the one obtained from Intoximeters, Inc. is preferred because of its high degree of accuracy in BAC determinations. Details regarding the construction and preparation of electrochemical fuel cells are believed to be well known, but can be found in a doctoral thesis submitted to the University of Wales by Michael John Henry Neame and is available from the British Library Document Supply Center.

The fuel cell 120 supplies an analog output signal on conductors 122 and 124. This signal is amplified, buffered and referenced to ground potential by a pair of conventional operational amplifiers 126 and 128. The resistors associated with the amplifiers 126 and 128 establish the gain and referencing functions. The output signal from the amplifier 128 is the gas detector signal at 24.

The output signal from the fuel cell 120 is a voltage which is related to the amount of alcohol contained in the breath sample conducted through the fuel cell 120. It has been determined that the accuracy of the signal supplied from the fuel cell 120 is measurably enhanced if, prior to conducting the sample into the fuel cell 120, the output terminals 122 and 124 of the fuel cell 120 are shorted to allow the electrochemical functions of the cell to stabilize at the lowest possible value. In order to short these terminals, a relay switch 130 is closed by current flowing through a relay coil 132. A transistor 134 is switched into a conductive state to conduct the current from the terminal 96 through the coil 132. A signal is applied at terminal 136 from the control interface 56 (FIG. 2) to control the conductive state of the transistor 134. In addition to providing more accurate readings, the momentary shorting of the output terminals 122 and 124 of the fuel cell 120 brings the output voltage of the fuel cell 120 to its lowest possible value at the start of the sampling process.

The pressure sensor 28 includes a conventional pressure transducer 140. The pressure transducer 140 selected for use in the present invention is one manufactured by Micro Switch, a division of Honeywell, Model No. PK 8766-2, although a variety of different conventional pressure transducers can be used. Electrical power for the pressure transducer 140 is supplied from terminal 92. The analog output signal from the pressure transducer 140 is applied to the input terminals of a conventional operational amplifier 142 which is connected to another operational amplifier 144. The operational amplifiers 142 and 144 buffer, reference with respect to ground, and amplify to a predetermined extent, the signal from the pressure transducer 140. The resistors and potentiometers associated with the amplifiers 142 and 144 aid in establishing these functions. The output signal from amplifier 144 is the pressure signal at 30.

The temperature sensor 32 includes a conventional fully integrated temperature sensor 146 which is connected to the electrical power terminal 92. The integrated temperature sensor 146 changes its current output in a predetermined relationship to the temperature it experiences, thereby providing a voltage signal which is proportional to temperature. Preferably the sensor 146 is located in the housing 12 to track as nearly as possible the temperature of the ambient air. The output signal from the sensor 146 is applied to an operational amplifier 148, where it is buffered, amplified and referenced to ground. The output signal from amplifier 148 is applied as the temperature signal at 34.

The battery sensor 64 is a voltage dividing network formed by resistors 150 and 152 which are connected in series and to the electrical power supply at terminal 92. The voltage at the junction of these resistors is applied as the low battery signal at 66. Of course, when the battery voltage diminishes, the voltage level at 66 also diminishes. When it is detected that the low voltage signal at 66 has diminished below a predetermined level, an indication will be displayed at the display 4 (FIG. 2). The display 44 is preferably of the liquid crystal type.

The multiplexer 60, the A to D converter 68, the processor 36 and the components of the main memory 38 are all conventional digital computer circuit elements. The communications interface 52 is preferably a conventional RS232 communications interface. The audio synthesizer 46 is also a conventional device, such as OKI Semiconductor MSM5205RS. The audio synthesizer 46 interfaces directly with the processor 36 over the bus 40, and converts the digital information stored in system memory 42 into synthesized speech, in accordance with the BAC information.

Details of the pump motor 110 are shown in FIG. 5. In general terms, the pump motor 110 is an electromagnetically reciprocated diaphragm pump which draws the breath sample into the inlet port 18, moves it through the fuel cell 120, and exhausts it out of the outlet port 116. The pump motor 110 can be made of very small dimensions which conveniently allows it to be incorporated within the housing 12 of the detector 10 (FIG. 1). In addition, the extent and rate of reciprocation is precisely controlled and is directly related to the volumetric gas flow conducted by the pump. Very precise volumetric flow rates are thereby established, and these volumetric flow rates are important in obtaining accurate BAC calculations.

The pump motor 110 includes an exterior plastic case portion 160, which is preferably made of NORELL. Within case portion 160 are positioned a pair of ferromagnetic cores 162 and 164 which, when positioned together, are generally C-shaped in cross section. Within the center of the cores 162 and 164 is an electrical coil 166. The terminal ends of the conductor of the coil 166 are connected to the terminal 92 and the transistor 112 (FIG. 4). A non-magnetic shaft 168 is positioned at the axis of the annular structure defined by cores 162, 164 and the coil 166. The shaft 168 is retained for axial movement by an opening in the case portion 160 at one end, and by another opening in an intermediate case portion 170 at the other end. The intermediate case portion 170 is also preferably made of plastic such as NORELL. In the mid-section of the shaft 168 is a shoulder 172. A ferromagnetic or other magnetic material bead or sleeve 174 is located between the shoulder 172 and the case portion 160. A spring 176 is positioned between the shoulder 172 and the opening in the case portion 170. The spring 176 normally biases the shaft to the left, as shown in FIG. 5. The length of the sleeve 174 establishes the maximum extent of leftward movement (as shown in FIG. 5) of the shaft 168.

When the coil 166 conducts current, the sleeve 174 is attracted toward the air gap between the cores 162 and 164. The attraction creates a force which is applied on the shoulder 172 to move the shaft 168 to the right, as shown in FIG. 5. When the current flow in the coil 166 is terminated, the spring 176 applies force on the shoulder 172 to force the shaft to the left, as shown in FIG. 5. Thus, when the coil 166 is energized, the shaft 168 is moved in one direction, and when the coil is de-energized, the spring 176 reciprocates the shaft in the opposite direction. In this manner, the shaft 176 is reciprocated in the pump motor 110.

A flexible pump diaphragm 180 is connected to one end of the shaft 168. A connector member 182 is connected to the end of the shaft 168, and a thrust washer 184 is connected to the connector member 182 by a screw 186. The diaphragm 180 is positioned between the connector member 182 and the thrust washer 184. The reciprocal movement of the shaft 168 deflects the diaphragm member 180. As is illustrated in FIG. 5, the diaphragm 180 is deflected as a result of the leftward position of the shaft 168. When the coil 166 is energized, the shaft 168 moves in the right direction as shown in FIG. 5.

The exterior edges of the diaphragm 180 are held in position by a compression block member 188 pressed by screws (not shown) against the intermediate case portion 170. The interior of the compression block member 188 and the diaphragm 180 define a pump chamber 190 through which the gas sample moves as the diaphragm member 180 is reciprocated. The interior of the intermediate case portion 170 defines an interior chamber 192 within which the connection member 182 moves. The chamber 192 is vented to the exterior of the pump motor 110 as a result of clearance between the shaft 168 and the openings through which it moves in the case portions 160 and 170.

A mounting block member 194 is connected to the compression block member 188, preferably by the same screws (not shown) which connect the member 188 to the case portion 170. The mounting block member 194 includes the appropriate passageways which connect the inlet port 18 with the interior of the fuel cell 120, and which conduct gas from the interior of the fuel cell 120 through the pump chamber 190 and out the exhaust port 116.

In order to obtain a pumping action, it is necessary to limit the gas flow to a single direction through the pump chamber 190. One way valves, such as flapper valves 196 and 198, are respectively positioned in the inlet 200 and outlet 202 of the pumping chamber 190. The flapper valves are also shown in FIG. 6. The flapper valves 196 and 198 work in the conventional manner to create one way gas flow through the pump chamber 190. During movement of the shaft 168 to the left (FIG. 5) to deflect the diaphragm 180 to expand the volume within the pumping chamber 190, the inlet flapper valve 196 is opened by the slight negative pressure within the pumping chamber 190 to allow gas to be drawn into the chamber 190 from the fuel cell 120 and inlet port 18. The slight negative pressure within the pumping chamber 190 holds the exhaust flapper valve 198 in a closed position, thereby assuring that gas is drawn through the inlet 200 into the pumping chamber 190 but not exhausted. When the shaft 168 moves in the other direction, to the right (FIG. 5), a slight positive pressure is created in the pumping chamber 190. The slight positive pressure closes the inlet flapper valve 196 and opens the exhaust flapper valve 198, thereby allowing the gas within the pumping chamber 190 to be pushed out through the outlet 202 to the exhaust port 116. When the flapper valves 196 and 198 are closed, they seat or set against surfaces on the mounting block 194 and the compression block member 188 to create a substantial fluid tight seal, in the conventional manner. When the flapper valves are opened, they are deflected off of the seating surfaces to allow space for gas to flow through the valves.

One of the desirable features of the pump motor 110 is its programably determinable flow rate, according to the frequency of electrical energization of the coil. Another advantage is its relative lack of moving parts, and thus its relative reliability. Its life expectancy is very high, compared to other types of pumps which require constant maintenance and replacement. The pump can be produced at a relatively low cost.

Details concerning the operation of the breath alcohol detector 10 are illustrated by the flow diagram shown in FIG. 7. Various steps or functions in the overall operation of the breath alcohol detector 10 are referenced by separate numerical references noted in FIG. 7.

The start of a BAC determination process is illustrated at 210. The switch 82 (FIG. 3) has previously been closed to energize the components of the detector. When a key from the key pad 14 (FIGS. 1 and 2) is pressed as shown at 212 the temperature will be measured at 214, the altitude or atmospheric pressure will be measured at 216, the pump motor will be activated at 218, and a distance measurement will be obtained at 220, as a result of the operation of the temperature sensor 34, the pressure sensor 28, the pump 20, and the distance sensor 26 (FIG. 2), respectively.

At least six distance measurements are achieved in 5 seconds as a result of the step at 224. The pump motor is deactivated after drawing the sample into the fuel cell, as is shown at 225. An average distance reading is obtained at 226 from the distance readings obtained at 224. By obtaining an average distance reading, variations in movement of the hand held detector 10 relative to the mouth of the individual being tested are averaged.

The algorithm used for obtaining each distance reading in inches is according to the following equation:
Distance $(D) = ((620 + t \times 0.000001) \times temp \times 0.61 \times 3310.1 m/sec)/2$, where "temp" is the temperature read at step 214 and "t" is the time in microseconds which is required for the reflected ultrasonic wave to be detected. "X" in the above equation signifies multiplication. In order to measure this time (t), the processor 36, as is shown in FIG. 2, sends a signal to the interface 62. The signal at the interface 62 is decoded and the drive signal is delivered to the distance sensor 26. The transducer disc is activated by the drive signal and transmits the outgoing ultrasonic wave. The disc is then used as a listening transducer and waits for the reflected ultrasonic wave. When the reflection is detected, the echo signal is delivered to the interface 62 and the interface 62 converts that signal to a signal applied to the processor 36. At the time the processor 36 delivers the signal for activating the sensor 26, it also starts an internal counter. When the echo signal is detected, the internal counter is stopped. The count recorded on the internal counter measures this time (t).

Referring back to FIG. 7, the fuel cell reading is next obtained at step 228. Of course, after the fuel cell reading, the temperature reading, the pressure reading and the average distance reading are obtained, they are recorded temporarily in RAM 50 (FIG. 2) to be used in the calculation of the blood alcohol content, which occurs at 230. The BAC information is displayed at 232 after each calculation at 230.

Because the fuel cell does not respond instantaneously to changes in the alcohol content of the sample, it is desirable to continue to obtain BAC information until the highest calcuation is obtained or until a particular time period has elapsed, as is illustrated at 234. After each BAC calculation has been obtained it is stored in RAM memory. Until the highest one has been obtained or an elapsed time has expired as shown at 234, the steps at 228, 230, and 232 are repeated.

To obtain the highest BAC information, a series of sequential BAC calculations are performed, each using a different fuel cell reading obtained at 228. The BAC information will usually increase in magnitude until the highest alcohol content signal from the fuel cell is obtained, and will thereafter decrease. The highest BAC information is detected when a plurality of subsequent BAC information calculations are obtained which are less than the highest BAC information which has been retained in memory. When this decrease is noted, the highest reading has been obtained and the calculation of further BAC information can be terminated. If the predetermined time established at 234 elapses and the BAC has remained the same, the highest BAC information is established and stored in memory and further calculations are terminated.

The algorithm used in calculating the blood alcohol content is as follows: $BAC = A \times V \times (1 + p + D)$. In this particular formula, "A" is a calibration factor obtained by calibrating the detector (discussed below in conjunction with FIG. 8, or the default value of 0.03077, if no calibration has occurred); "V" is the change in voltage of the fuel cell, i.e. the maximum voltage attained less the start voltage; "D" is the distance in inches, the calculation of which has been previously described, and "p" is a diffusion factor intended to compensate for temperature and pressure. The diffusion factor is established by the following formula: $p = 0.847619 \times (12/press) \times (TO + T/TO)^{3/2} \times 1/\Omega(t')$. In the diffusion factor formula, "press" is the measured atmospheric pressure; "TO" is 273.15 degrees K.; "T" is the measured temperature in degrees C.; ("t'") is $TO + T/168.8$; and "Omega" is $0.6024 + (0.6433/t')$. "X"s indicate a multiplication operation.

An audible warning may be delivered at 237 after the highest or timed out BAC information has been established at 234. Both the fact and type of audible warning to be delivered at 237 can be determined by the BAC information. For example, the audible warning may instruct the individual to repeat the test by moving closer to the detector and counting while the test progresses. Another audible warning may simply be a direct indication that the subject is intoxicated. The warnings may include additional warnings to the effect of advising the individual not to drive an automobile or the like. Many other types of audible warnings are available as a result of programming standard warnings into memory for synthesis by the audio synthesizer 46 (FIG. 2).

Once the highest BAC reading has been determined, it is stored in memory 38 (FIG. 2) as well as the date and time when that reading was obtained, as is illustrated at 236. However, before storing this highest BAC reading, the fuel cell shorting switch 130 (FIG. 4) is closed at 238 for a period of 45 seconds established at 240, and is thereafter opened at 242. The steps 238, 240 and 242 assure that the fuel cell is returned to its lowest stabilized reading at the conclusion of calculating the highest BAC reading, thereby readying the detector at step 244 for starting the next breath alcohol content calculation at 210. By calculating the BAC using the relative voltage change or differential between the beginning and end points, it is unnecessary to wait for the fuel cell to return to a predetermined low voltage point before commencement of the next BAC determination. As a consequence, a greater number of complete tests can be accomplished in the same relative time and with increased accuracy as compared to prior breathalyzers.

By storing the BAC readings at the time and date in step 236, this information can later be retrieved for use as legal evidence or for other purposes. The readings can be displayed on the display 44 of the detector 10 (FIG. 1) or they can be conducted from the computer system of the detector 10 through the communications interface 52 to another computer or other device where that information is utilized.

By calculating the average distance reading between the subject's mouth and the detector of the present invention, the diffusion of the exhaled breath sample into the surrounding environmental ambient air can be accounted for in calculating the BAC. This is a significant improvement, since the information obtained more reliably correlates to the actual blood alcohol content of the individual. This also increases the convenience of use, because the person being subjected to the test does not have to directly breathe into a breath tube or other receptacle. It allows law enforcement officers and others to obtain information without actually having to physically contact the person with the equipment or otherwise.

In the case of an electrochemical fuel cell, the consumption of alcohol from the sample is related to the amount of oxygen in the ambient air. The oxygen content of the ambient air is related to the atmospheric pressure or altitude. By measuring the atmospheric pressure, it is possible to compensate for varying oxygen levels. The significance of this compensation is that recalibration is unnecessary in accounting for different geographic locations and weather conditions.

Ambient temperature measurements sensed may be used to further compensate for the upward drift of exhaled breath due to buoyancy effects. For example, the cone shaped expulsion of breath at about body temperature will rise much faster in lower ambient air temperature than in higher ambient air temperature, thus also affecting the diffusion of the exhaled breath into the ambient air. The temperature measurements are also used to compensate the distance measurements to account for the differences in the speed of the ultrasonic waves through the air at different temperatures.

Shorting the fuel cell before calculating each BAC, and obtaining the highest BAC reading increases the accuracy and reliability of the present invention. Precisely regulating the volumetric gas flow through the fuel cell as a result of the operation of the pump motor also contributes significantly to the increased reliability of data obtained from the breath alcohol detector of the present invention.

The need for recalibration has proved to be one of the substantial disadvantages of many prior alcohol content detectors. Rather elaborate calibration procedures have been required to assure that the information supplied by such detectors accurately represents the probable blood alcohol content. The detector 10 of the present invention lends itself to a convenient and accurate self-calibration procedure, as is illustrated in FIG. 8. The self-calibration procedure is intended to compensate for fuel cell deviation. The calibration technique is performed under the control of calibration software recorded in memory of the detector.

The operator starts the calibration procedure at 300 by depressing a calibration key at 302 on the keyboard 14 (FIG. 2). The temperature is next read at 304, followed by the atmospheric pressure at 306. At the start of the calibration procedure the operator sprays a standard vapor phase solution of alcohol (ethanol) into the intake port 18 (FIGS. 1 and 2). This standard solution is preferably a predetermined standard solution, for example 0.020% alcohol. The sample motor is next activated at 308 which draws the standard sample into the fuel cell. A five second running time of the sample motor, established at 310, assures that the standard sample is drawn into the fuel cell. Operation of the pump motor is thereafter terminated at 311. A fuel cell reading is thereafter obtained at 312, and additional fuel cell readings are obtained as a result of the operation at 314 until the highest fuel cell reading has been obtained. Once the highest fuel cell reading has been obtained at 314, the fuel cell shorting relay is activated at 316 and is held in the activated position for 45 seconds as is shown at 318. Thereafter, the shorting relay is deactivated at 320.

A calibration factor is calculated at 322 before the end at 324 of the calibration procedure. The calibration factor is used in the algorithm which calculates the blood alcohol content (BAC). The calibration factor is used in each BAC calculation and is retained in memory until the detector is recalibrated and a newly calculated calibration factor is obtained. The equation for calculating the calibration factor is $A = B/V$, where B is the 0.020 ethanol alcohol standard used for calibration, i.e. 0.020% ethanol alcohol at a distance of zero inches; and V is the peak fuel cell voltage read when performing a calibration.

As a result of the convenient self-calibration process described above, the expense, inconvenience and potential risk of inaccuracy associated with frequent, complex recalibrations by skilled technicians using complicated equipment is avoided. This achieves a significant improvement over prior breath alcohol content detectors.

Although the preferred embodiment of the present invention has been discussed in the context of a breath alcohol detector, it can also be employed more generally as a gas content detector. When used as a gas content detector, the fuel cell is selected to be responsive to the selected type of gas. Usually it will be unnecessary to determine and compensate for distance since the sample will generally permeate the ambient environment uniformly. However, if the selected gas is diffusing from a point source, diffusion compensation may be retained. Of course, different gas content algorithms will be employed in the gas content calculations.

The presently preferred embodiment of the present invention has been shown and described with a degree of particularity, but it should be understood that the scope of the invention is defined in the following claims.

What is claimed is:

1. A breath alcohol detector for use in obtaining blood alcohol content information of an individual from a sample of breath exhaled by the individual into ambient air, comprising:
   means for collecting a sample of exhaled breath which has been diffused into the ambient air at a location spaced apart from the mouth of an individual;
   means for deriving an alcohol content signal related to the quantity of alcohol present in the collected sample;
   means for deriving a distance signal related to the distance at which the sample was collected from the mouth of the individual; and
   means for calculating a value representative of the blood alcohol content of the individual utilizing the alcohol content signal and the distance signal in the calculation.

2. A breath alcohol detector as defined in claim 1, further comprising:
   means for deriving a temperature signal related to the temperature of the ambient air; and wherein:
   said means for calculating the value representative of the blood alcohol content of the individual also utilizes the temperature signal in the calculation.

3. A breath alcohol detector as defined in claim 1 wherein:
   said means for deriving a distance signal derives a plurality of individual distance signals; and further comprising:
   means for averaging the individual distance signals to obtain an average distance signal; and wherein:
   said means for calculating a value representative of the blood alcohol content of the individual also utilizes the average distance signal in the calculation.

4. A breath alcohol detector as defined in claim 1, further comprising:
   means for deriving a pressure signal related to the atmospheric pressure of the ambient air; and wherein
   said means for calculating the value representative of the blood alcohol content of the individual also utilizes the pressure signal in the calculation.

5. A breath alcohol detector as defined in claim 4, further comprising:
   means for deriving a temperature signal related to the temperature of the ambient air; and wherein:
   said means for calculating the value representative of the blood alcohol content of the individual also utilizes the temperature signal in the calculation.

6. A breath alcohol detector as defined in claim 1, further comprising:
   memory means for retaining the value representative of the blood alcohol content for later retrieval and use.

7. A breath alcohol detector as defined in claim 6, further comprising:
   clock means for supplying a time signal indicative of the time when the blood alcohol content value was calculated, and wherein:
   said memory means also retains the time signal and blood alcohol content value in association with one another.

8. A breath alcohol detector as defined in claim 1, wherein:
   said means for deriving an alcohol content signal derives a plurality of sequential alcohol content signals;
   said means for calculating the value representative of the blood alcohol content of the individual calculates a plurality of values each of which represents the blood alcohol content of the individual based on a corresponding one of the plurality of sequential alcohol signals; and further comprising:
   means for determining the greatest one in magnitude of the plurality of blood alcohol content values derived; and
   means for supplying the one of the blood alcohol content values which is the greatest in magnitude.

9. A breath alcohol detector as defined in claim 8, further comprising:
   means for terminating the calculation of the blood alcohol content values upon detecting a predetermined decrease in the magnitude of blood alcohol content values relative to at least one prior derived blood alcohol content value.

10. A breath alcohol detector as defined in claim 9, wherein:
    said means for terminating the calculation upon detecting a predetermined decrease does so when a predetermined plurality of blood alcohol content values are less in magnitude than the blood alcohol content value of the greatest magnitude.

11. A breath alcohol detector as defined in claim 1, wherein:
    said means for deriving an alcohol content signal comprises an electrochemical fuel cell; and
    said means for collecting the sample further includes pumping means for moving the sample collected into the fuel cell.

12. A breath alcohol detector as defined in claim 11 wherein:
    the electrochemical fuel cell supplies an output signal related to the amount of alcohol present in the collected sample,
    the alcohol content signal is related to the relative difference in the output signal from the fuel cell when exposed to the collected sample, and
    said means for calculating a value representative of the blood alcohol content of the individual does so based on the relative difference of the output signal of the fuel cell without requiring the output signal from the fuel cell to diminish to a predetermined initial level before commencement of another different determination of blood alcohol content information.

13. A breath alcohol detector as defined in claim 11, wherein said pumping means further comprises:
    reciprocal acting motor means, and
    a diaphragm pump operatively driven by said motor means.

14. A breath alcohol detector as defined in claim 13, wherein:

the reciprocal acting motor means comprises a shaft retained for reciprocal movement, a magnetic member attached to the shaft, an electromagnetic means positioned for attracting the magnetic member to move the shaft in one reciprocal direction when the electromagnetic means is energized, and means for moving the shaft in an opposite reciprocal direction when the electromagnetic means is not energized; and the diaphragm pump comprises a flexible diaphragm operatively connected with the shaft so as to be deflected upon reciprocal movement of the shaft, and means defining a pumping chamber in which the volume of the chamber varies in relation to the deflection of the diaphragm; and further comprising:

means for energizing the electromagnetic means at a predetermined rate to reciprocate the shaft and deflect the diaphragm at related predetermined rates to obtain a predetermined volumetric flow through the pumping chamber.

15. A breath alcohol detector as defined in claim 14, wherein:

the diaphragm pump further comprises an inlet to the pumping chamber, an inlet one way valve which allows the sample to enter the pumping chamber and prevents gas flow through the inlet out of the pumping chamber, an outlet from the pumping chamber, and an outlet one way valve which allows the sample to exit the pumping chamber and prevents gas flow through the outlet into the pumping chamber.

16. A breath alcohol detector as defined in claim 15, wherein:

the inlet and the outlet one way valves are each flapper valves.

* * * * *